(12) United States Patent
Hughes

(10) Patent No.: US 8,773,484 B2
(45) Date of Patent: Jul. 8, 2014

(54) METHOD AND APPARATUS FOR MARKING A LABORATORY SAMPLE CASSETTE

(76) Inventor: Thomas Fergus Hughes, Netherfield (GB)

( * ) Notice: Subject to any disclaimer, the term of this patent is extended or adjusted under 35 U.S.C. 154(b) by 0 days.

(21) Appl. No.: 13/808,227

(22) PCT Filed: Jul. 6, 2011

(86) PCT No.: PCT/GB2011/051268
§ 371 (c)(1),
(2), (4) Date: Mar. 17, 2013

(87) PCT Pub. No.: WO2012/004596
PCT Pub. Date: Jan. 12, 2012

(65) Prior Publication Data
US 2013/0162744 A1     Jun. 27, 2013

(30) Foreign Application Priority Data

Jul. 6, 2010 (GB) .................................. 1011317.3

(51) Int. Cl.
*B41J 2/325* (2006.01)
*B41F 16/00* (2006.01)

(52) U.S. Cl.
USPC .......................................... 347/171; 347/110

(58) Field of Classification Search
USPC ................................................. 347/171, 110
See application file for complete search history.

(56) References Cited

U.S. PATENT DOCUMENTS

| 7,009,630 | B1 | 3/2006 | Finger et al. |
| 7,094,732 | B2 | 8/2006 | Finger |
| 7,163,728 | B2 | 1/2007 | Finger |
| 2008/0044587 | A1 | 2/2008 | Maeno et al. |
| 2008/0055385 | A1 | 3/2008 | Houjou |
| 2008/0136892 | A1 | 6/2008 | Doi et al. |
| 2009/0167835 | A1 | 7/2009 | Hughes |
| 2011/0187806 | A1* | 8/2011 | Hughes ..................... 347/171 |

FOREIGN PATENT DOCUMENTS

| GB | 2 235 163 A | 2/1991 | |
| WO | WO 2010/032045 | * 3/2010 | ................ B01L 3/00 |

OTHER PUBLICATIONS

PCT/GB2011/051268 International Search Report, mailed Nov. 2, 2011.
GB 1011317.3 Search Report under Section 17, dated Nov. 3, 2010.

* cited by examiner

*Primary Examiner* — Huan Tran
(74) *Attorney, Agent, or Firm* — Fay Sharpe LLP

(57) ABSTRACT

In order to mark a laboratory sample cassette (2), dye marks (40, 41) are printed by an inkjet printer head (7) onto a tape (11). Rollers (17) move the tape (11) from a first location (13) adjacent to the printer head (7) to a cassette receiving location (15). A cassette clamp marker (8) at the cassette receiving location (15) has a shaped member (10) arranged to fold the tape (11) when a laboratory sample cassette (2) is in the cassette receiving location (15) so that part of the tape (11) covers a marking surface (6) of the cassette (2) and another part of the tape (11) covers a side surface (4) of the cassette (2). The shaped member (10) also has heating pads (26, 29) and when an actuator (32) applies the shaped member (10) to the tape (11) in the cassette receiving location (15), the heating pads (26, 29) are heated so that dye of the dye marks (40, 41) on the tape (11) ingresses into the marking surface (6) and the side surface (4) of the cassette (2) to mark these surfaces.

15 Claims, 5 Drawing Sheets

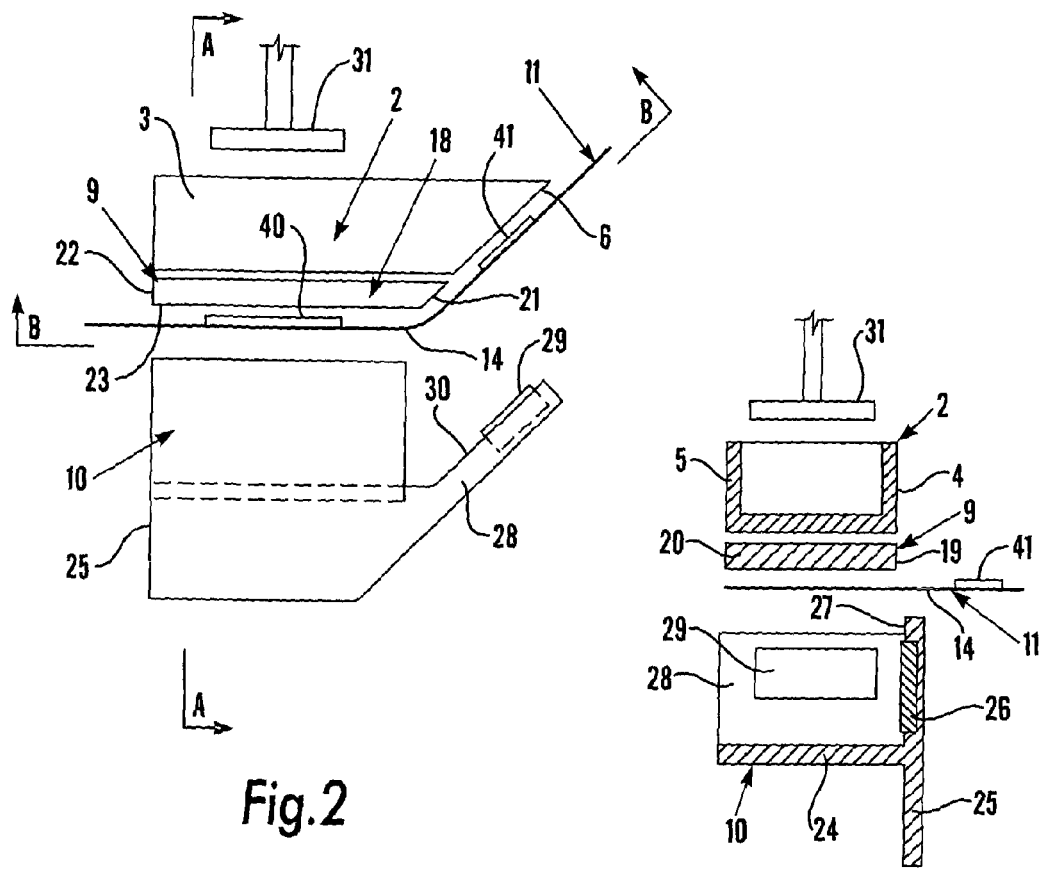
Fig.2
Fig.3
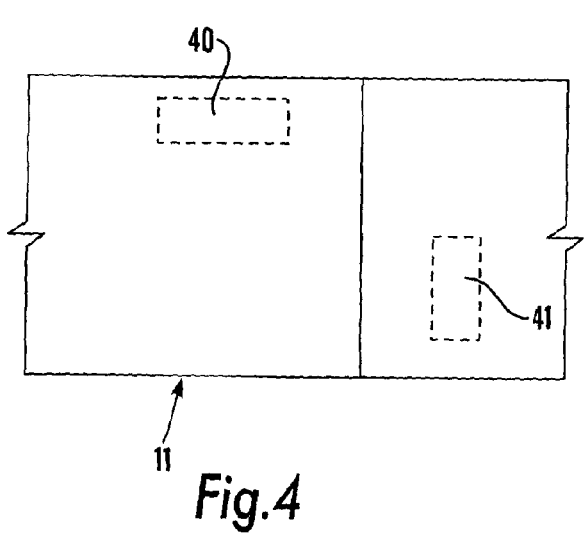
Fig.4

METHOD AND APPARATUS FOR MARKING A LABORATORY SAMPLE CASSETTE

This application is a national filing under 35 U.S.C. 371 of International Application Number PCT/GB2011/051268, International Filing date 6 Jul. 2011, which claims the priority benefit of GB Patent Application No. 1011317.3, filed 6 Jul. 2010.

The present invention relates to a method and apparatus for marking a laboratory sample or tissue cassette.

A laboratory sample cassette has a marking or writing surface disposed at an inclined angle of typically 45° to a main rectangular body of the cassette. The cassette is of plastic and forms a tray to hold a sample or tissue for processing, and the cassette has a removable lid. After processing, the cassette also acts as a support mould for a wax block containing the processed sample.

One method of marking laboratory sample cassettes involves hot foil printing technology to print the required marking or text onto the marking surface. Another method involves the marking surface of the cassette being given a covering or a coating and using a laser to burn away part of the covering to create the required marking or text.

A problem with the hot foil printing and laser methods is that the marked marking surface is susceptible to damage caused by abrasion or a scalpel so that the mark may be damaged or removed. This may occur when surplus wax is removed from at least the marking surface of the cassette as part of the cassette processing and is a very common cause of damage to printed cassettes.

Another problem is that the size of the marking surface of the laboratory sample cassette limits the amount of information that can be printed on the cassette.

It is an object of the present invention to provide a method and apparatus to alleviate at least one of the above-mentioned problems.

According to one aspect of the present invention there is provided a method of marking a laboratory sample cassette, comprising:
(a) depositing dye on a tape;
(b) moving the tape between heating means and at least one surface of a laboratory sample cassette to be marked so that dye on the tape is adjacent said at least one surface;
(c) heating the heating means; and
(d) applying the heated heating means to the tape so that dye from the tape ingresses into the at least one surface to be marked to mark said at least one surface.

By the dye ingressing or penetrating into the surface(s) of the cassette, the marked surface(s) becomes very resistant to surface abrasion and is permanently protected from the chemicals and solvents that may be applied to the laboratory sample cassette during its processing. It is the surface material itself that protects the dye which has ingressed into it.

The method produces high print quality and enables full colour printing. The ability to print in colour reduces the need for pre-coloured cassettes to distinguish between them. Thus, the user can use only white colour cassettes and different coloured cassettes are not required. This drastically reduces the inventory and also eliminates the situation of a user selecting the wrong coloured cassette for printing.

Dye ingressing or penetrating into the surface(s) of the cassette may be achieved by dye sublimation or dye being vaporised by the heating means.

The method may include the step of folding the tape so that at least part of the tape covers at least parts of a plurality of surfaces of the cassette, each said surface being adjacent and facing in a different direction to at least one other said surface, and step (d) causes a plurality of said surfaces of the cassette to be marked by dye from said tape ingressing into said plurality of surfaces. Thus, if any surfaces of the cassette in addition to the main cassette marking surface is marked, more information can be printed on the cassette, and surfaces formed in different directions can be marked thereby enabling cassettes stacked in different directions to be readily identifiable.

Step (a) may comprise applying at least one dye mark to said tape, and wherein step (d) causes the at least one surface to be marked to be marked by dye from said at least one dye mark ingressing into said at least one surface. The at least one dye mark may be applied to the tape by ink jet printing.

The tape may be clamped between the heating means and the at least one surface of the cassette to be marked. This may cause the tape folding step so that at least part of the tape covers at least part of said plurality of surfaces of the cassette to be marked. The clamping step may cause the heated heating means to be applied to the cassette so that said plurality of surfaces to be marked is marked by dye from said tape ingressing into said surfaces. Thus, the plurality of surfaces are marked simultaneously.

A dye mark may be applied to said tape for each said surface of the cassette to be marked so that when said tape is folded each said surface is arranged to be marked by its respective dye mark. If the same information was to be written on different surfaces of the cassette by hand a mistake could easily be made. The method enables the same information to be applied simultaneously to different surfaces removing the risk of such a mistake being made.

A plurality of laboratory sample cassettes may be marked, and step (a) includes depositing dye on a plurality of tapes arranged substantially parallel to each other, each tape with deposited dye being used to mark a respective cassette. The plurality of said laboratory sample cassettes may be arranged to be marked simultaneously.

According to another aspect of the present invention there is provided an apparatus for marking a laboratory sample cassette, comprising
dye depositing means for depositing dye onto a tape;
tape moving means adapted to move the tape from a first location adjacent to the dye depositing means to a second location between heating means and a laboratory sample cassette at a laboratory sample cassette receiving location;
tape folding means arranged to fold the tape when a laboratory sample cassette is in the cassette receiving location so that at least part of the tape is adapted to cover at least part of a plurality of surfaces of the cassette, each said surface being adjacent and facing in a different direction to at least one other said surface; and
actuating means for applying heating means to said tape in the cassette receiving location so that when the heating means is heated dye from the tape ingresses into a plurality of said surfaces to mark said plurality of surfaces.

The apparatus may include clamping means to clamp the tape between the heating means and the surfaces of the cassette to be marked when the cassette is in the cassette receiving location. The clamping means may include a shaped member comprising tape folding means, and the tape folding means includes said heating means.

A plurality of tapes arranged substantially parallel to each other, and a corresponding plurality of laboratory sample cassette receiving locations. The dye depositing means may be arranged to be moved from one tape to another so as to deposit dye on a plurality of the parallel tapes. The tape moving means may be arranged to move each tape independently of the other tapes. This maximises throughput of cassettes to be marked and provides flexibility.

Embodiments of the present invention will now be described, by way of example, with reference to the accompanying schematic drawings, in which:

FIG. 2 is a side view of a cassette clamp marker of the apparatus in an open position;

FIG. 3 is a sectional view taken along lines A-A of FIG. 2;

FIG. 4 is a bottom view of a portion of a marked tape in the cassette clamp marker in the open position and is taken along lines B-B of FIG. 2;

Figure 1:
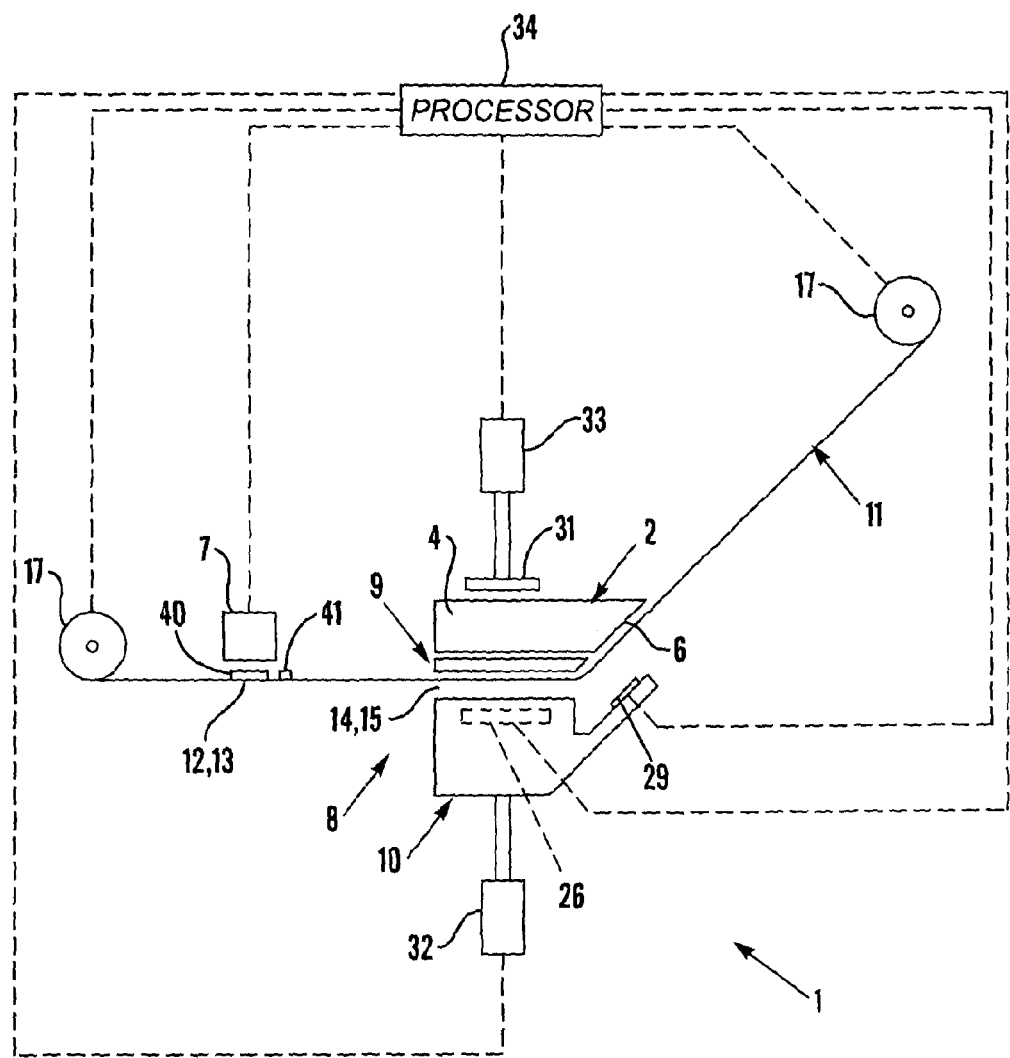
FIG. 1 is a view of an apparatus for marking a laboratory sample cassette according to one embodiment of the invention.

Referring to FIGS. 1 to 3 of the accompanying drawings, an apparatus 1 is arranged to mark a laboratory sample or tissue cassette 2 having a main rectangular body 3 forming a tray with opposing first and second side surfaces 4, 5 and a marking or writing surface 6 between the side surfaces 4, 5 and disposed at an inclined angle to the main rectangular body 3.

The apparatus 1 has an inkjet printer with a print head 7, and a cassette clamp marker 8. The cassette clamp marker 8 has a support 9 for receiving a laboratory sample cassette 2 and a shaped member 10 positioned beneath the support 9.

A tape 11 has a fixed width and has a first portion 12 at a first location 13 positioned beneath the print head 7. The tape 11 also has a second portion 14 at a second location 15 in the cassette clamp marker 8 and part of the second portion 14 is positioned between the support 9 and the shaped member 10. Tape rollers 17 move the tape 11 from the first location 13 to the second location 15.

The support 9 comprises a rectangular plate 18 with opposing first and second side edges 19, 20 and opposing end edges 21, 22. Each end edge 21, 22 is perpendicular to the tape 11 and one end edge 21 is disposed at an inclined angle to a lower face 23 of the plate 18 at the same angle as the marking surface 6 of the cassette 2 that the apparatus 1 is to mark. The second tape portion 14 is adjacent both the lower face 23 and the inclined edge 21 so that the second tape portion 14 is bent round the plate 18. The second tape portion 14 is positioned such that part of its width extends beyond the support plate first side edge 19.

The shaped member 10 has a horizontal plate 24 parallel to the support plate 18 and the horizontal plate 24 extends from the side of a vertical plate 25 which is positioned just beyond the support plate first side edge 19. A heat pad 26 is placed in a recess in a face 27 of the vertical plate 25 above the horizontal plate 24 of the shaped member 10 so that the pad 26 does not extend substantially beyond the face 27. The shaped member 10 also has a plate 28 parallel to the support plate inclined end edge 21. A heat pad 29 is placed in a recess in an upper inclined face 30 of the plate 28 so that the pad 29 does not extend substantially beyond the face 30.

A clamp member 31 is positioned above the support 9, and actuators 32, 33 are arranged to drive the shaped member 10 and the clamp member 31 towards each other.

An electronic control processor 34 is connected to, and controls, the heat pads 26, 29, the actuators 32, 33, the inkjet print head 7, and tape rollers 17.

In use, the cassette clamp marker 8 is set in an open position in which the shaped member 10 is spaced from the support 9 and the clamp member 31 is spaced above the support 9 so that a cassette 2 can be received. A laboratory sample cassette 2 is dropped onto the support 9 so that its marking surface 6 is aligned with the support plate inclined end edge 21 and is adjacent the second tape portion 14. The first side surface 4 of the cassette 2 is also aligned with the support plate first side edge 19.

An operator or user of the apparatus 1 selects a first mark 40, such as an image/text or a barcode, to be marked on the first side surface 4 of the laboratory sample cassette 2 and a second mark 41 to be marked on the inclined marking surface 6 of the cassette 2. The tape first portion 12 opposite the inkjet print head 7 has the marks 40, 41 formed by dye droplets printed on it by the inkjet print head 7 using a dye sublimation ink which the tape 11 is treated to accept. The second mark 41 is printed across the tape 11 and the first mark 40 is printed so that it is perpendicular to the second mark 41 (see FIG. 4).

The first tape portion 12 with the dye marks 40, 41 is moved by the rollers 17 until the tape portion 12 is partly between the laboratory sample cassette 2 on the support 9 and the shaped member 10 so that the first mark 40 is parallel to and beyond the support plate first side edge 19 and the second mark 41 is facing the cassette marking surface 6.

Figure 5:
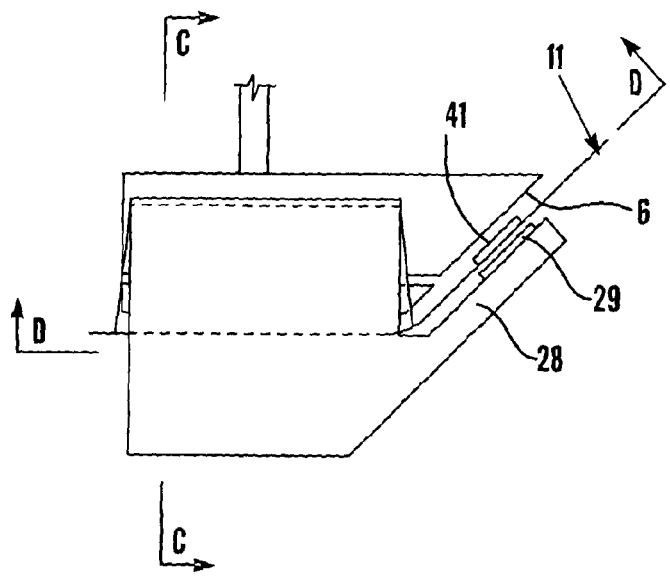
FIG. 5 is a side view of the cassette clamp marker in a closed position.
Figure 6:
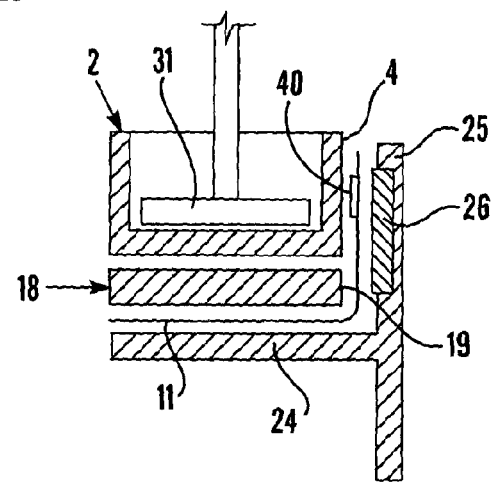
FIG. 6 is a sectional view taken along lines C-C of FIG. 5.
Figure 7:
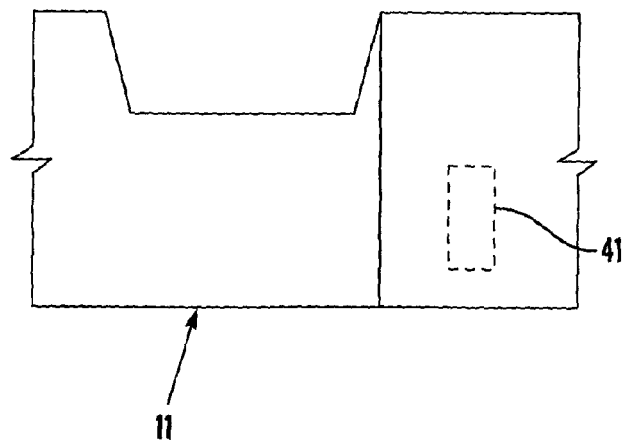
FIG. 7 is a bottom view of a portion of a marked tape in the cassette clamp marker in the closed position and is taken along lines D-D of FIG. 5.
Figure 8:
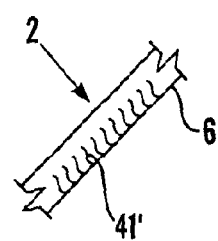
FIG. 8 is a sectional view of part of a marked cassette.

Referring to FIGS. 5 to 7, the heat pads 26, 29 of the shaped member 10 are heated and the shaped member and the clamp member actuators 32, 33 are actuated which causes the shaped member 10 and the clamp member 31 to be moved towards one another. As the shaped member 10 is moved upwards, its vertical plate 25 causes the portion of the tape 11 containing the first mark 40 to be folded against the support plate first side edge 19 and the cassette first side surface 4, and the inclined plate 28 of the shaped member 10 presses the tape 11 against the inclined marking surface 6 of the cassette 2. As the clamp member 31 is moved downwards it enters the cassette tray and when it reaches the tray bottom the clamp member holds the cassette 2 against the support plate 16. The clamp member 31 is also moved laterally slightly so that the cassette first side surface 4 presses the tape 11 against the shaped member vertical plate 25. The heated pads 26, 29 of the shaped member 10 are aligned with the first and second dye marks 40, 41 so that the first dye mark 40 is applied to the first side surface 4 of the cassette 2 and the second dye mark 41 is applied to the marking surface 6 of the cassette 2. The cassette clamp marker 8 is thus now in a closed position. The pressure and heat of the pads 26, 29 causes the dye to vapourise and ingress into the cassette first side surface 4 and cassette marking surface 6 (see FIG. 8) thus marking the cassette 2 and the mark applied to the first side surface 4 and the mark 41' applied to the marking surface 6 are protected by the material of the surfaces 4, 6. The dye may penetrate up to 0.25 mm into the surface.

The shaped member 10 and the clamp member 31 are then moved away from each other so that the cassette clamp marker 8 is returned to its open position. The tape 11 is moved by the tape rollers 17 and the part of the first tape portion 12 adjacent the inclined marking surface 6 of the cassette 2 causes the cassette 2 to be pulled away from the support 9 and drop out of the apparatus 1. Another cassette for marking is then dropped onto the now empty support 9. The linear action of marking successive cassettes increases print throughput which is important for busy laboratories.

The above embodiment enables two adjacent surfaces 4, 6 of a cassette 2 to be marked by dye from the tape 11 ingressing into the surfaces 4, 6. If the cassette 2 is to have the same mark on two adjacent surfaces 4, 6 then the first and second marks 40, 41 on the tape 11 may be reverse or mirror images of each other. The first and second dye marks 40, 41 may adjoin when the tape 11 is folded. This enables a cassette 2 to be marked by, say, an image which is bent around the edge between two adjacent surfaces of the cassette 2.

Figure 9:
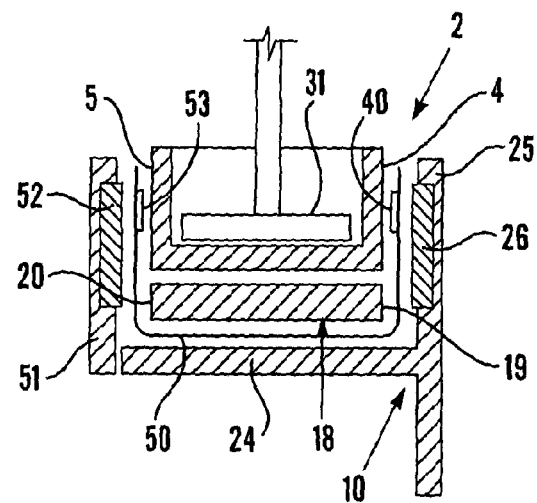
FIG. 9 is a sectional view of a modified cassette clamp marker in a closed position.

In a modification illustrated in FIG. 9, the tape 50 is of a sufficient width that it extends beyond both the support plate first and second side edges 19, 20. A member 51 containing another heat pad 52 can be applied to the second side surface 5 of the cassette 2 so that a portion of the tape 50 can be folded against the second side surface 5. This tape portion also has a dye mark 53 applied to it so that the second side surface 5 can also be marked.

Figure 10:
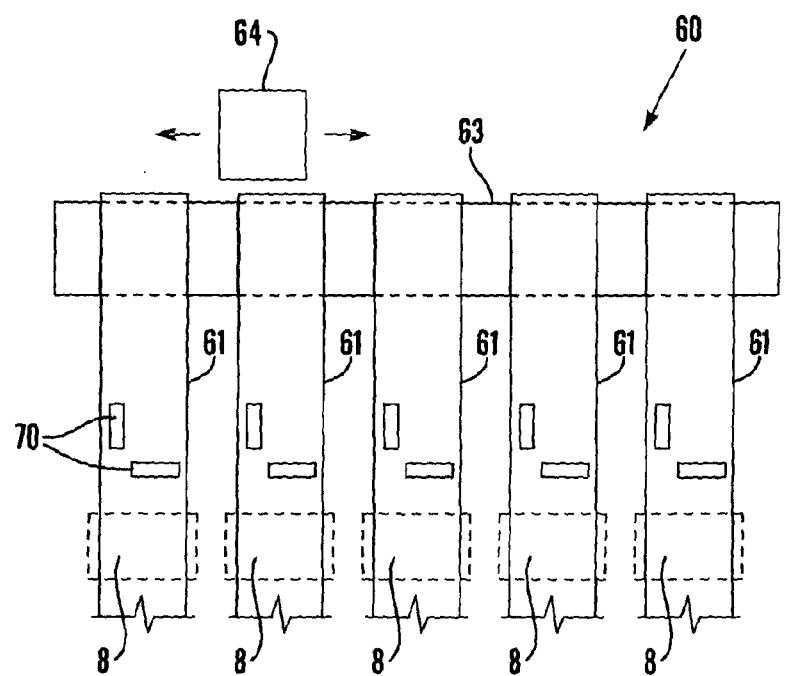
FIG. 10 is a plan view of part of an apparatus for marking a laboratory sample cassette according to another embodiment of the invention.
Figure 11:
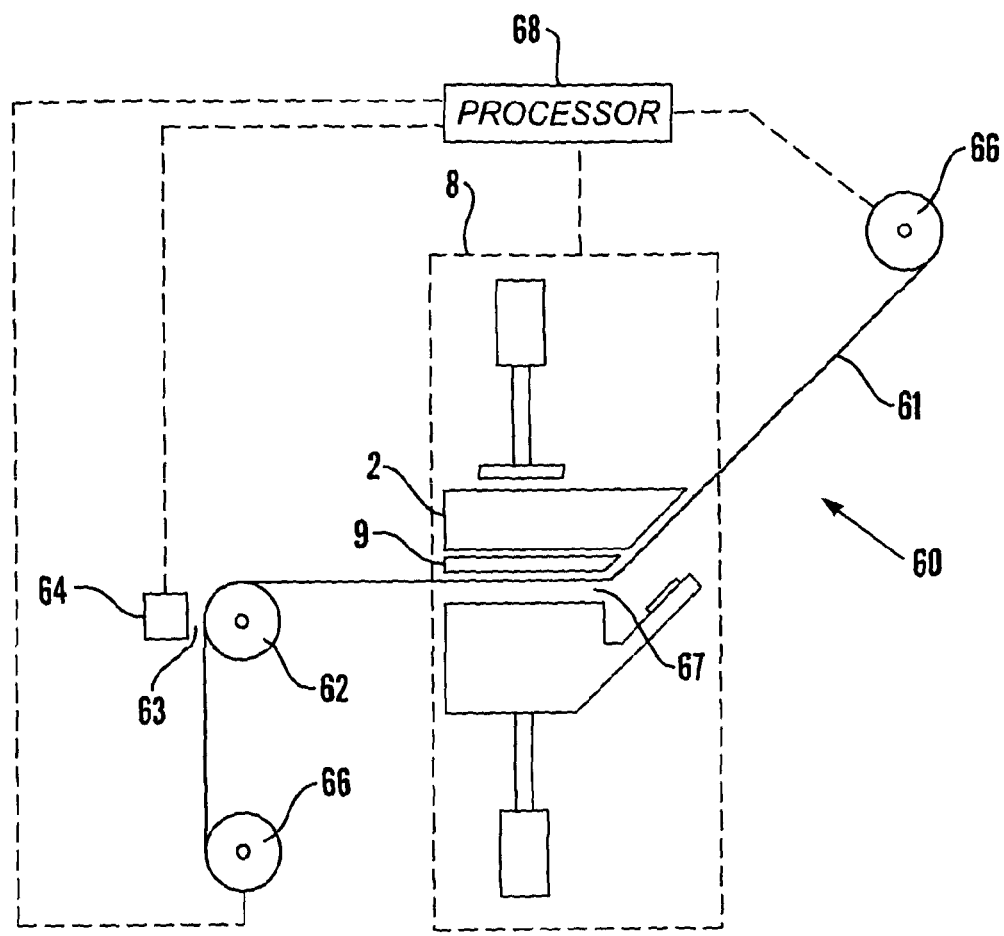
FIG. 11 is a side view of the apparatus of FIG. 10.

Referring to FIGS. 10 and 11, an apparatus 60 for marking a plurality of laboratory sample cassettes 2 includes a plurality of tapes 61 arranged parallel to each other and a first portion of each tape 61 is wrapped around a common round or cylindrical inkjet printer platen 62 forming the first location 63. The print head 64 of the inkjet printer is arranged to be moved from one tape 61 to another so as to print dye marks 70 on any number of the parallel tapes 61. Rollers 66 are used to move each tape 61 independently of the other tapes. A second portion of each tape 61 is at a second location 67 at a support 9 of a corresponding cassette clamp marker 8. The support 9 is arranged to be able to receive a laboratory sample cassette 2 for each corresponding tape 61 and the cassettes 2 are marked by respective cassette clamp markers 8 in the same way as previously described. A central processor 68 is connected to, and controls, the inkjet print head 64, the tape rollers 66 and the cassette clamp marker 8 for each tape 61.

The central processor 68 determines how many tapes 61 should be printed and what information is to be printed. The marking information or data for each corresponding cassette 2 is processed and batched so that the print head 64 is moved to print the required marks or images on the selected tapes. A cassette 2 is orientated so that it drops onto the second location 67 for each printed tape. The portion of each tape with print 70 is moved by the rollers 66 until the tape portion is at the respective second location 67. The cassettes 2 are then marked with the print at their second location 67 simultaneously. The portion of the tapes adjacent the inclined marking surface 6 of the cassettes 2 causes the marked cassettes to be pulled away from their second location 67 and released to a user of the apparatus 60.

The apparatus 60 is shown as having five tapes. If a user requires four cassettes to printed simultaneously then the inkjet printer head 64 is directed to print on four of the five tapes. The four marked tapes are then moved to their respective second locations and a cassette at each second location 67 is duly marked and then released to the user.

Whilst particular embodiments have been described, it will be understood that various modifications may be made without departing from the scope of the invention.

What is claimed is:

1. A method of marking a laboratory sample cassette, comprising:
    (a) depositing dye on a tape;
    (b) moving the tape between a heater and a plurality of surfaces of a laboratory sample cassette to be marked so that dye on the tape is adjacent said plurality of surfaces;
    (c) heating the heater;
    (d) folding the tape so that at least part of the tape covers at least part of a plurality of surfaces of the cassette, each said surface being adjacent and facing in a different direction to at least one other said surface; and
    (e) applying the heated heater to the tape so that dye from the tape ingresses into the plurality of surfaces to be marked to mark said plurality of surfaces.

2. The method as claimed in claim 1, wherein step (a) comprises applying at least one dye mark to said tape, and wherein step (e) causes the plurality of surfaces to be marked to be marked by dye from said at least one dye mark ingressing into said plurality of surfaces.

3. The method as claimed in claim 1, wherein a dye mark is applied to said tape for each said surface of the cassette to be marked so that when said tape is folded each said surface is arranged to be marked by its respective dye mark.

4. The method as claimed in claim 1, including the step of clamping the tape between the heater and the plurality of surfaces of the cassette to be marked.

5. The method as claimed in claim 4, wherein the clamping step causes the tape folding step so that at least part of the tape covers at least part of said plurality of surfaces of the cassette to be marked.

6. The method as claimed in claim 5, wherein the clamping step causes the heated heater to be applied to the cassette so that said plurality of surfaces to be marked is marked by dye from said tape ingressing into said surfaces.

7. The method as claimed in claim 1, wherein a plurality of laboratory sample cassettes are marked, and step (a) includes depositing dye on a plurality of tapes arranged substantially parallel to each other, each tape with deposited dye being used to mark a respective cassette.

8. The method as claimed in claim 7, wherein the plurality of said laboratory sample cassettes are arranged to be marked simultaneously.

9. An apparatus for marking a laboratory sample cassette, comprising
    a dye depositor for depositing dye onto a tape;
    a tape mover adapted to move the tape from a first location adjacent to the dye depositor to a second location between a heater and a laboratory sample cassette at a laboratory sample cassette receiving location;
    a tape folder arranged to fold the tape when a laboratory sample cassette is in the cassette receiving location so that at least part of the tape is adapted to cover at least part of a plurality of surfaces of the cassette, each said surface being adjacent and facing in a different direction to at least one other said surface; and
    an actuator for applying the heater to said tape in the cassette receiving location so that when the heater is heated dye from the tape ingresses into a plurality of said surfaces to mark said plurality of surfaces.

10. The apparatus as claimed in claim 9, including a clamp to clamp the tape between the heater and the surfaces of the cassette to be marked when the cassette is in the cassette receiving location.

11. The apparatus as claimed in claim 10, wherein the clamp includes a shaped member comprising the tape folder, and the tape folder includes said heater.

12. The apparatus as claimed in claim 9, including a plurality of tapes arranged substantially parallel to each other, and a corresponding plurality of laboratory sample cassette receiving locations.

13. The apparatus as claimed in claim 12, wherein the dye depositor is arranged to be moved from one tape to another so as to deposit dye on a plurality of the parallel tapes.

14. The apparatus as claimed in claim 13, wherein said tape mover is arranged to move each tape independently of the other tapes.

15. The apparatus as claimed in claim 9, wherein the heater includes first and second heat pads so that dye from the tape is transferred to separate first and second surfaces of the plurality of surfaces of the cassette.

* * * * *